United States Patent
Mansour et al.

(10) Patent No.: US 11,814,956 B2
(45) Date of Patent: Nov. 14, 2023

(54) SYSTEM AND METHODOLOGY FOR DETERMINING PHASE TRANSITION PROPERTIES OF NATIVE RESERVOIR FLUIDS

(71) Applicant: Schlumberger Technology Corporation, Sugar Land, TX (US)

(72) Inventors: Sophie Mansour, Cairo (EG); Shu Pan, Sugar Land, TX (US); Younes Jalali, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 110 days.

(21) Appl. No.: 16/764,510

(22) PCT Filed: Nov. 16, 2018

(86) PCT No.: PCT/US2018/061429
§ 371 (c)(1),
(2) Date: May 15, 2020

(87) PCT Pub. No.: WO2019/099770
PCT Pub. Date: May 23, 2019

(65) Prior Publication Data
US 2020/0355072 A1 Nov. 12, 2020

Related U.S. Application Data

(60) Provisional application No. 62/587,063, filed on Nov. 16, 2017.

(51) Int. Cl.
*E21B 49/08* (2006.01)
*G01N 33/28* (2006.01)

(52) U.S. Cl.
CPC ........ *E21B 49/0875* (2020.05); *E21B 49/081* (2013.01); *G01N 33/2823* (2013.01)

(58) Field of Classification Search
CPC .... E21B 49/0875; E21B 49/081; E21B 49/10; G01N 33/2823
See application file for complete search history.

(56) References Cited

U.S. PATENT DOCUMENTS

| 6,274,865 B1 * | 8/2001 | Schroer | G01N 21/3577 250/269.1 |
| 7,081,615 B2 * | 7/2006 | Betancourt | E21B 47/10 250/255 |

(Continued)

OTHER PUBLICATIONS

International Preliminary Report on Patentability issued in the PCT Application PCT/US2018/061429, dated May 28, 2020 (11 pages).

(Continued)

*Primary Examiner* — Jennifer H Gay
(74) *Attorney, Agent, or Firm* — Jeffrey D. Frantz (57) ABSTRACT

A technique facilitates fluid analysis in situ at a downhole location. According to an embodiment, a sample of fluid, e.g. oil, is obtained from a reservoir at the downhole location in a borehole. A downhole sampling system is used to determine contamination of the sample of fluid and to determine other selected characteristics of the sample. The data obtained is then processed to determine a true phase transition property of a native fluid in the sample of fluid. The sample analysis may be performed at selected stations along the borehole during, for example, a well cleanup operation. The immediate analysis of fluid samples downhole facilitates rapid development of an understanding of fluid characteristics in the reservoir, thus enabling an improved oil recovery strategy.

17 Claims, 5 Drawing Sheets

(56) References Cited

U.S. PATENT DOCUMENTS

| | | | | |
|---|---|---|---|---|
| 7,695,629 B2* | 4/2010 | Salamitou | E21B 43/38 | 210/321.75 |
| 7,784,330 B2* | 8/2010 | Angelescu | G01N 11/08 | 73/54.09 |
| 7,920,970 B2 | 4/2011 | Zuo et al. | | |
| 8,335,650 B2* | 12/2012 | Hsu | G01N 33/2823 | 73/152.55 |
| 8,434,356 B2* | 5/2013 | Hsu | E21B 47/113 | 175/48 |
| 8,434,357 B2* | 5/2013 | Hsu | E21B 49/08 | 73/152.24 |
| 8,805,617 B2* | 8/2014 | Zuo | E21B 49/08 | 702/179 |
| 9,051,821 B2* | 6/2015 | Tan | E21B 49/081 | |
| 9,255,475 B2* | 2/2016 | Zuo | E21B 49/10 | |
| 10,073,042 B2* | 9/2018 | Wang | G01N 21/8507 | |
| 10,132,164 B2* | 11/2018 | Dumont | E21B 49/10 | |
| 10,208,591 B2* | 2/2019 | Smythe | E21B 49/08 | |
| 10,280,745 B2* | 5/2019 | Eyuboglu | E21B 49/087 | |
| 10,316,656 B2* | 6/2019 | Zuo | E21B 49/088 | |
| 10,352,160 B2* | 7/2019 | Pop | E21B 49/081 | |
| 2004/0104341 A1* | 6/2004 | Betancourt | G01N 1/12 | 250/255 |
| 2009/0030858 A1* | 1/2009 | Hegeman | G06N 3/02 | 166/264 |
| 2009/0183871 A1* | 7/2009 | Salamitou | E21B 49/10 | 210/652 |
| 2010/0147065 A1* | 6/2010 | Tan | E21B 47/10 | 73/152.24 |
| 2011/0042070 A1* | 2/2011 | Hsu | E21B 49/08 | 702/85 |
| 2011/0042071 A1* | 2/2011 | Hsu | E21B 49/08 | 166/250.01 |
| 2011/0088895 A1* | 4/2011 | Pop | E21B 49/087 | 166/254.2 |
| 2011/0088949 A1* | 4/2011 | Zuo | E21B 49/10 | 175/48 |
| 2011/0093200 A1* | 4/2011 | Hsu | G01N 33/2823 | 702/12 |
| 2013/0188169 A1* | 7/2013 | Harrison | G01N 21/85 | 356/36 |
| 2013/0239664 A1* | 9/2013 | Hsu | E21B 49/087 | 73/54.02 |
| 2013/0311099 A1* | 11/2013 | Eyuboglu | E21B 49/081 | 702/11 |
| 2014/0238122 A1 | 8/2014 | Mostowfi et al. | | |
| 2014/0260586 A1* | 9/2014 | Van Hal | E21B 49/082 | 73/152.11 |
| 2014/0268156 A1* | 9/2014 | Smythe | G01N 21/59 | 356/436 |
| 2015/0211363 A1* | 7/2015 | Pop | E21B 49/081 | 73/152.28 |
| 2015/0308264 A1* | 10/2015 | Zuo | E21B 49/088 | 702/6 |
| 2015/0354345 A1* | 12/2015 | Meier | E21B 49/10 | 73/1.16 |
| 2017/0146688 A1* | 5/2017 | Sugiyama | G01F 1/8472 | |
| 2017/0175521 A1* | 6/2017 | Pirolli | E21B 49/08 | |
| 2017/0175522 A1* | 6/2017 | Smythe | G01N 9/002 | |
| 2017/0370215 A1* | 12/2017 | Hsu | E21B 49/10 | |
| 2019/0145242 A1* | 5/2019 | Jalali | E21B 49/088 | 166/250.01 |
| 2020/0355072 A1* | 11/2020 | Mansour | G01N 33/2823 | |
| 2021/0263008 A1* | 8/2021 | Jalali | E21B 47/00 | |

OTHER PUBLICATIONS

International Search Report and Written Opinion issued in the PCT Application PCT/US2018/061429, dated Feb. 25, 2019 (15 pages).
Substantive Examination Report issued in Saudi Arabian Patent Application No. 520411979 dated Oct. 12, 2022, 20 pages with English translation.

* cited by examiner

SYSTEM AND METHODOLOGY FOR DETERMINING PHASE TRANSITION PROPERTIES OF NATIVE RESERVOIR FLUIDS

CROSS-REFERENCE TO RELATED APPLICATIONS

This application claims priority to and the benefit of US Provisional Application having Ser. No. 62/587,063, filed 16 Nov. 2017, which is incorporated by reference herein.

BACKGROUND

Hydrocarbon fluids such as oil and natural gas are obtained from a subterranean geologic formation, referred to as a reservoir, by drilling a well that penetrates the hydrocarbon-bearing geologic formation. During and/or after this drilling process, fluid samples are taken along the wellbore to determine characteristics of the hydrocarbon fluid contained in the reservoir. The fluid samples may be tested to determine various characteristics of both the fluid and the reservoir. Knowledge regarding those characteristics can be useful in optimizing production from the reservoir. Some testing is performed downhole while other samples are retrieved to the surface for laboratory analysis.

SUMMARY

In general, a methodology and system are provided to facilitate fluid analysis in situ at a downhole location. According to an embodiment, a sample of fluid, e.g. oil, is obtained from a reservoir at the downhole location in a borehole. A downhole sampling system is used to determine contamination of the sample of fluid and to determine other selected characteristics of the sample. The data obtained is then processed to effectively determine a phase transition property of an uncontaminated sample of the fluid. The sample analysis may be performed at selected stations along the borehole during, for example, a well cleanup operation. The immediate analysis of fluid samples downhole facilitates rapid development of an understanding of fluid characteristics in the reservoir, thus enabling an improved oil recovery strategy.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a methodology and system to facilitate fluid analysis in situ at a downhole location. The methodology and system may be used for analyzing oil samples at a plurality of stations along a borehole drilled into an oil bearing formation. According to an embodiment, each sample of oil is obtained from a reservoir via a downhole sampling system deployed to desired downhole locations. The downhole sampling system may comprise a contamination monitoring module used to determine elements of contamination in each sample of fluid, e.g. each sample of oil from the surrounding reservoir. Use of the contamination monitoring module enables compensation with respect to testing of other selected characteristics of the sample using, for example, a microfluidic module.

The data obtained from the modules may be processed to determine a true phase transition property of a fluid, e.g. native oil, within each sample of fluid. The sample analysis may be performed at selected stations along the borehole during, for example, a well cleanup operation. The immediate analysis of fluid samples downhole facilitates rapid development of an understanding of fluid characteristics in the reservoir. The newfound understanding may then be used to enable creation of an improved oil recovery strategy.

The sampling system may be deployed downhole into a borehole, e.g. a wellbore, as part of a well string. By way of example, the sampling system may be deployed downhole via tubing, wireline, or another suitable conveyance. According to embodiments, the sampling system may be employed for downhole fluid analysis during well cleanup operations and/or during other suitable downhole operations, such as wireline operations and while-drilling operations.

In general, the sampling system may be used to obtain measurements in situ for downhole fluid analysis so as to obtain desired physical properties of reservoir fluid, e.g. physical properties which would otherwise be determined via laboratory procedures. As described in greater detail below, the sampling system may be used for downhole fluid sampling and analysis of oil and gas samples. The downhole, in situ analysis is performed to provide data used to obtain information on the desired physical property. The desired physical property may be a phase transition property of the native reservoir fluid, such as a phase transition property related to bubble point pressure (BPP), dew point pressure (DPP), asphaltene onset pressure (AOP), and/or other phase transition property.

According to an embodiment of the methodology, two measurement systems are used together to obtain desired information about the nature of a native reservoir fluid without capturing and delivering fluid samples to a laboratory. By obtaining this information during fluid sampling operations, the measurement program of the well being sampled can be influenced. For example, the measurement program can be adjusted when the in situ analysis reveals the potential presence of specific fluid intervals in a fluid column above or below and observed interval. As a result, stations at shallower or deeper depths than the interval observed can be investigated for confirmation of the total fluid column. If a well trajectory precludes such an investigation, the intervals can be explored by sidetracks or by subsequently drilled wells. The information regarding makeup of the fluid column can be obtained via the sampling system even if no samples are captured for laboratory analysis.

The two measurement systems may be used with specific and independent functions. For example, one measurement system may be used to determine a purity level of the effluent flowing from the formation. The effluent may comprise a mixture of native reservoir fluid and non-reservoir fluid used during drilling operations, e.g. drilling mud. The purity refers to the fraction that is native reservoir fluid. The other measurement system may be used to capture the effluent and to measure its phase transition properties using, for example, depressurization. The depressurization process may involve determining the pressure when oil begins to give off gas (bubble point pressure) or the pressure when gas begins to give off liquid (dew point pressure). Each of the measurement systems may comprise sensors to determine desired parameters, e.g. density, viscosity, temperature, pressure, of the fluid samples so as to facilitate the determination of desired fluid properties.

Data from the two measurement systems may be combined to yield the desired phase transition properties of the native reservoir fluid as opposed to properties of the contaminated fluid comprising both native reservoir and non-reservoir fluids. The phase transition properties are obtained by following a procedure of data acquisition at each measurement station during, for example, a well cleanup operation. The well cleanup operation may occur during a period when the well is flowed to purge as much of the non-reservoir fluids as possible, a process known as back-flow. However, the measurement systems also may be used to obtain data during other well operations.

The in situ operational procedure coupled with in situ data analysis procedures as described herein yield the desired phase transition properties of the native reservoir fluid. The phase transition properties may be determined regardless of whether one or several instances of sample measurement are performed with respect to the contaminated reservoir fluid during a well cleanup operation or other well related operation. The phase transition properties also may be obtained based on the in situ procedures and analysis regardless of whether water-based mud or oil-based mud is used during the corresponding drilling operation. The phase transition properties also may be determined by utilizing sampling modules with unfocused techniques having one flow line or focused techniques having two flow lines through which the reservoir sample is directed. The in situ sampling procedures and analysis ensures a rapid turnaround with respect to results which can be used to, for example, optimize well fluid production models.

Depending on the application, various types of phase transition properties may be determined, e.g. determined at selected stations along the borehole. For example, embodiments described herein may comprise determining phase transition properties in the form of bubble point pressure which is the pressure at which oil begins to give off gas when depressurization happens at a constant temperature equal to the formation temperature. However, the sampling techniques disclosed herein also may be used to determine phase transition properties of dew point pressure which is a pressure at which gas begins to give off dew or liquid. The sampling techniques also may be used to determine other phase transition properties, such as asphaltene onset pressure.

Figure 1:
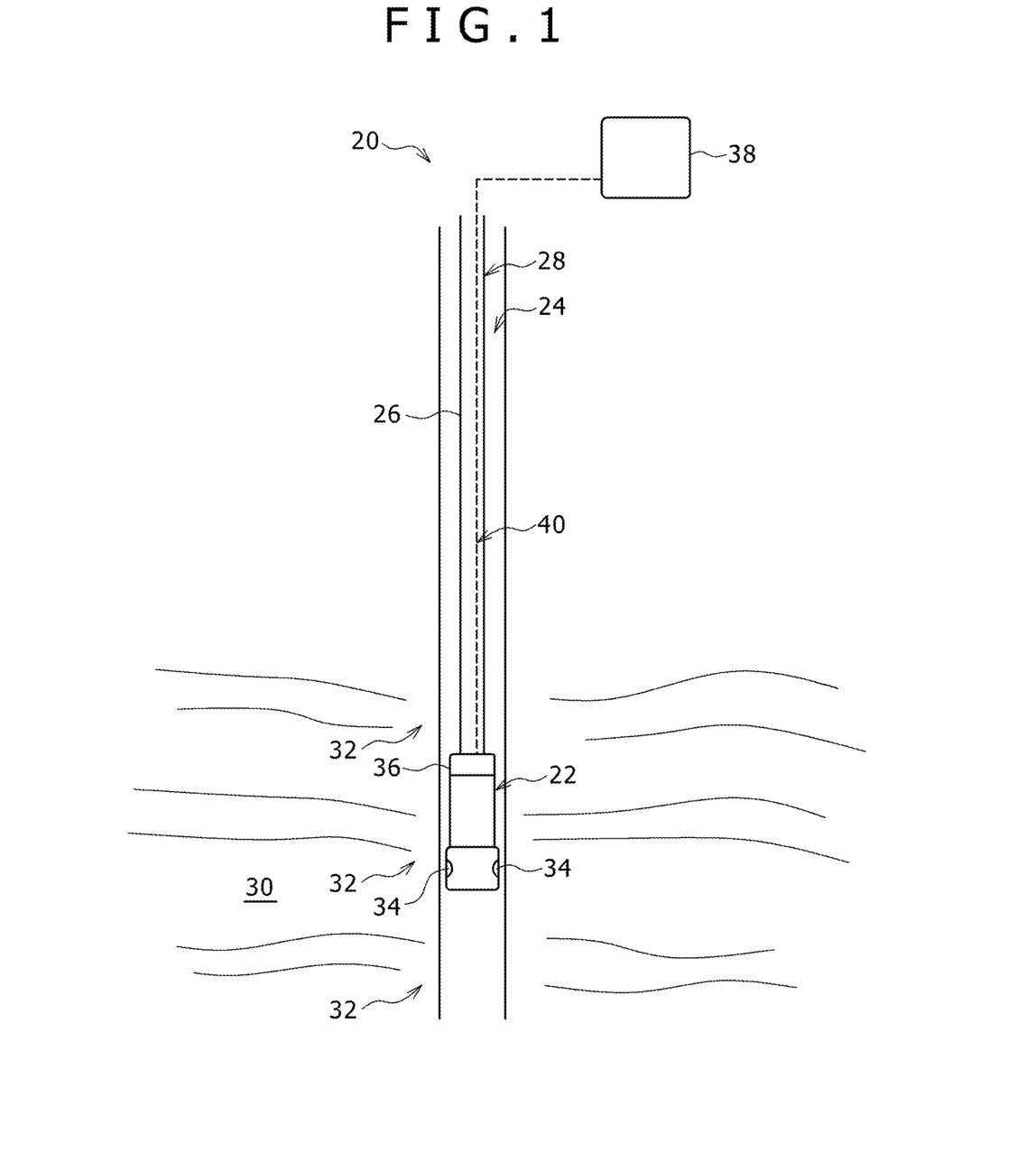
FIG. 1 is a schematic illustration of an example of a well system comprising a sampling system deployed downhole in a borehole, according to an embodiment of the disclosure.

Referring generally to FIG. 1, an example of a well system 20 is illustrated. In this embodiment, the well system 20 comprises a sampling system 22 which may be conveyed downhole into a borehole 24, e.g. a wellbore, via a conveyance 26. The conveyance 26 may comprise tubing, e.g. production tubing or coiled tubing, wireline, or another suitable conveyance.

Additionally, the sampling system 22 and conveyance 26 may be part of an overall well string 28 having various other components selected for a given operation. For example, the well string 28 may comprise a drill string and sampling system 22 may be used to obtain well fluid samples, e.g. oil samples, during a cleanup operation following drilling a borehole 24. The well string 28 also may be used during other types of well operations.

The sampling system 22 is moved to a desired location along borehole 24 so as to obtain a sample of fluid, e.g. oil, which enters borehole 24 from a reservoir 30 in the surrounding subterranean geologic formation. In various applications, the sampling system 22 may be moved via conveyance 26 to a plurality of different stations 32 along borehole 24 for analysis of a given fluid sample or samples. The fluid samples, e.g. oil samples, may be taken at selected stations 32 for in situ analysis downhole. The sampling system 22 may comprise or work in cooperation with PVT (pressure/volume/temperature) sensors 34, e.g. pressure and temperature sensors, to monitor pressures and temperatures at the various formation stations 32.

The property related data provided via the in situ analysis by sampling system 22 may be processed further to determine the desired well fluid/oil property, e.g. the true bubble point pressure of the native oil or other phase transition properties. The further processing of the property data from sampling system 22 may be performed downhole, at the surface, or partially downhole and partially at the surface. In some applications, the processing may be done at least in part via a downhole processor 36 operatively coupled with sampling system 22. The sampling system 22 also may be coupled with a surface processing system 38 via a suitable telemetry system 40, e.g. a wired or wireless telemetry system. In some applications, both the downhole processor 36 and the surface processing system 38 may be utilized in processing data provided via the in situ analysis performed by downhole sampling system 22.

Figure 2:
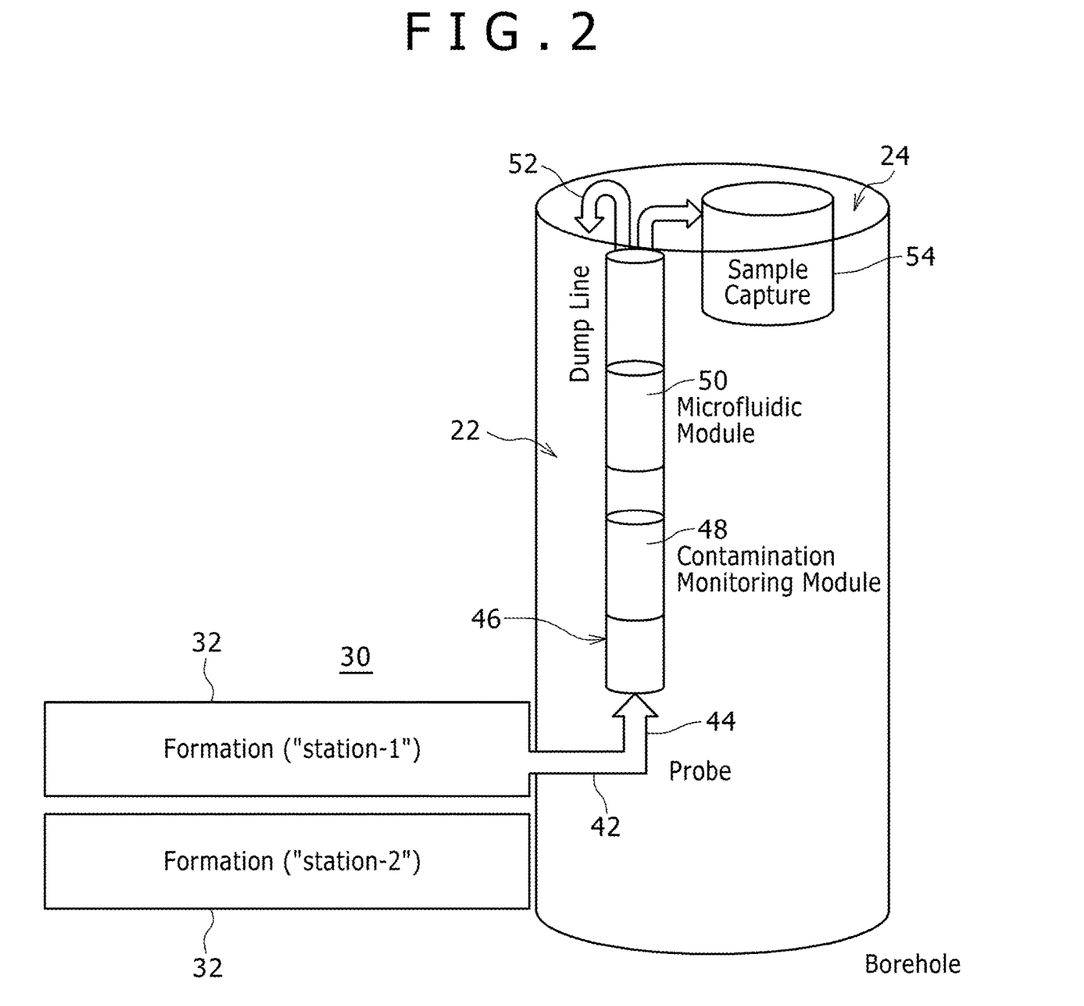
FIG. 2 is a schematic illustration of an example of a sampling system for testing fluid samples in situ within the borehole, according to an embodiment of the disclosure.

Referring generally to FIG. 2, an example of sampling system 22 is illustrated. In this embodiment, sampling system 22 is deployed in wellbore 24 proximate the first formation station 32 of a plurality of stations 32. The sampling system 22 comprises a probe 42 through which a sample of fluid 44, e.g. a sample of oil, is drawn from the surrounding formation/reservoir 30. The sample 44 flows into a sampling system structure 46, e.g. a housing or manifold, for analysis via appropriate fluid analysis modules.

The fluid analysis modules may be selected to, for example, analyze each sample 44 in situ to correct for contamination and to provide other sample characteristics used to determine the desired phase transition property, e.g. bubble point pressure. By way of example, the sampling system 22 may comprise a contamination monitoring module 48 and a microfluidic measurement module 50. In this example, each sample 44 flows through probe 42, into structure 46, and into contamination monitoring module 48 for in situ detection and correction due to contamination of the sample 48, e.g. oil sample, so as to facilitate further analysis. For example, the contamination monitoring module 48 may be used to obtain data which is processed to correct for the presence of non-native reservoir fluids in the sample 44.

In the illustrated embodiment, the sample 44 continues to flow through structure 46 and into microfluidic measurement module 50. The microfluidic measurement module 50 is then used in situ to determine other desired characteristics of the sample 44 so as to enable determination of the bubble point pressure and/or other phase transition property of the sample 44 via the data obtained from the downhole analysis. Data resulting from the in situ analysis at contamination monitoring module 48 and microfluidic measurement module 50 may be provided to the processing system, e.g. downhole processor 36 and/or surface processing system 38, to determine the bubble point pressure and/or other phase transition property. In the specific example illustrated, each sample 44 may be further directed through structure 46 and flowed into, for example, a dump line 52 and/or sample capture chamber 54.

Figure 3:
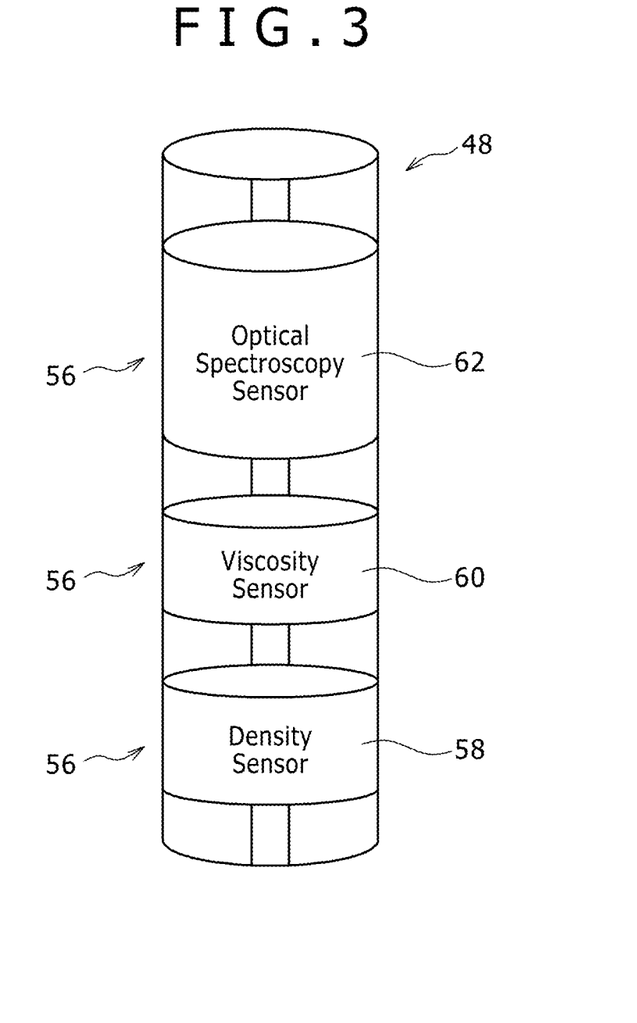
FIG. 3 is a schematic illustration of an example of a contamination monitoring module which may be employed in the sampling system, according to an embodiment of the disclosure.
Figure 4:
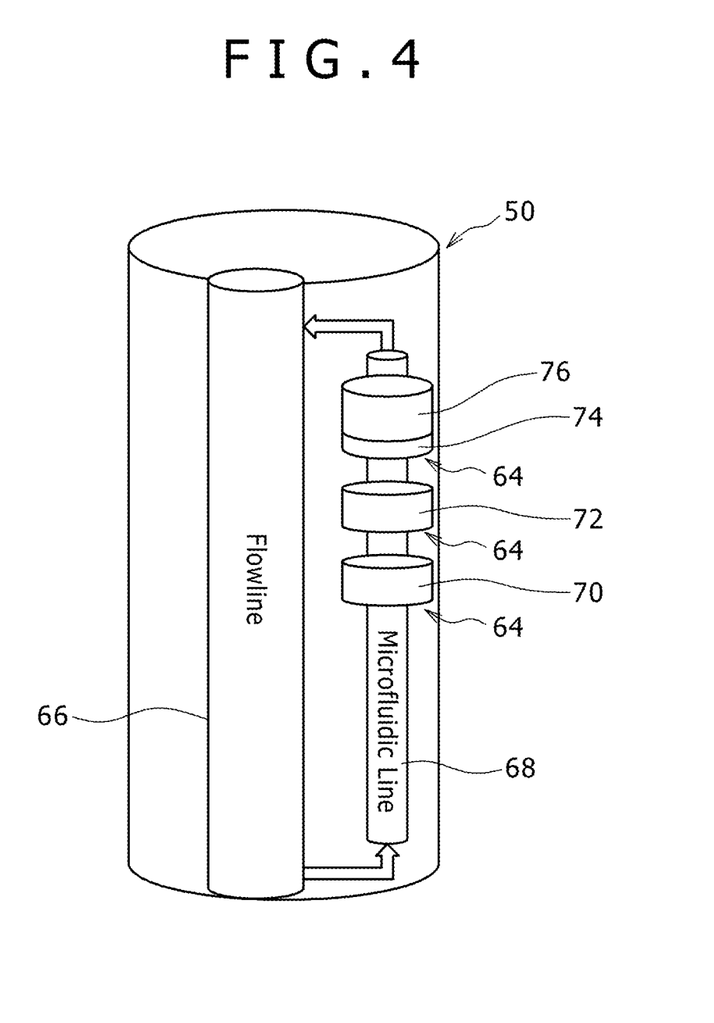
FIG. 4 is a schematic illustration of an example of a microfluidic module which may be employed in the sampling system, according to an embodiment of the disclosure.

Referring generally to FIGS. 3 and 4, examples of contamination monitoring module 48 and microfluidic measurement module 50, respectively, are illustrated. As illustrated in FIG. 3, the contamination monitoring module 48 may comprise a plurality of sensors 56 arranged to detect specific characteristics of each sample 44 so as to provide data on contaminating constituents, e.g. non-native reservoir fluid, within the sample 44. By way of example, the contamination monitoring module 48 may comprise sensors 56 in the form of a density sensor 58, a viscosity sensor 60, and an optical spectroscopy sensor 62.

These sensors 56 may be used individually or in combination to obtain data indicative of contaminants within the oil sample 44 obtained from the corresponding station 32. The contamination monitoring module 48 may be constructed for focused sampling, e.g. dual flow line sampling, or unfocused sampling, e.g. single flow line sampling. The embodiment illustrated shows the contamination monitoring module 48 as an unfocused sampling module with a single probe and single flow line but the module 48 may be constructed for more advanced monitoring via, for example, focused sampling with two probes and two flow lines. It should be noted the sensors 56 also may comprise pressure and/or temperature sensors 34 or data may be obtained from separate pressure and/or temperature sensors 34.

In some applications, the optical spectroscopy sensor 62 may be in the form of an optical module having a light source and corresponding detectors. The detectors work in cooperation with the light source to scan flowing fluid at different wavelengths as the sample 44 flows through contamination monitoring module 48. The data obtained from scanning the sample fluid at different wavelengths may be used to determine basic chemical ingredients of the fluid stream, e.g. methane, ethane, propane, butane, and/or other ingredients. From this chemical information, other properties may be inferred such as gassiness of the oil resulting from the gas-oil-ratio (GOR). Such properties are useful in determining the presence of contaminants, such as non-reservoir fluid.

As illustrated in FIG. 4, the microfluidic measurement module 50 also may comprise a variety of sensors 64 selected to obtain data which can be processed to determine the desired phase transition property of each sample 44 from selected formation stations 32. In the example illustrated, the microfluidic measurement module 50 comprises a primary flow line 66 and a microfluidic line 68 with sensors 64 disposed along the microfluidic line 68. By way of example, sensors 64 may comprise a density sensor 70, a viscosity sensor 72, and an optical spectroscopy sensor 74 which cooperates with a depressurization chamber 76. The primary flow line 66 may extend through both contamination monitoring module 48 and microfluidic module 50 for delivering the sample from probe 42, through module 48, 50, and then to an appropriate discharge.

The depressurization chamber 76 may be operated to provide controlled depressurization of each sample 44, e.g. to enable determination of the bubble point pressure and/or other desired phase transition property. Phase transition property related data obtained from the in situ analysis performed at microfluidic module 50 may be further processed via the processing system 36 and/or 38 to accurately determine the desired phase transition property of the uncontaminated fluid. It should be noted that sensors 56 and/or 64 also may comprise pressure and temperature sensors 34 for monitoring downhole conditions. In some applications, the pressure and temperature sensor 34 may be separate from sampling system 22 but operatively coupled with downhole processor 36 and/or surface processing system 38.

As illustrated, the sample 44, e.g. oil sample, flows from primary flow line 66, into microfluidic line 68, through sensors 64 and back into the primary flow line 66. Data obtained in situ via the flow of fluid samples through contamination monitoring module 48 and microfluidic module 50 of sampling system 22 may be processed to determine the true phase transition properties of the native oil in the formation/reservoir 30. The data also may be used to determine changes in the phase transition properties at the different stations 32 along borehole 24. A procedure for determining the desired phase transition properties, e.g. bubble point pressure, is provided below.

Figure 5:
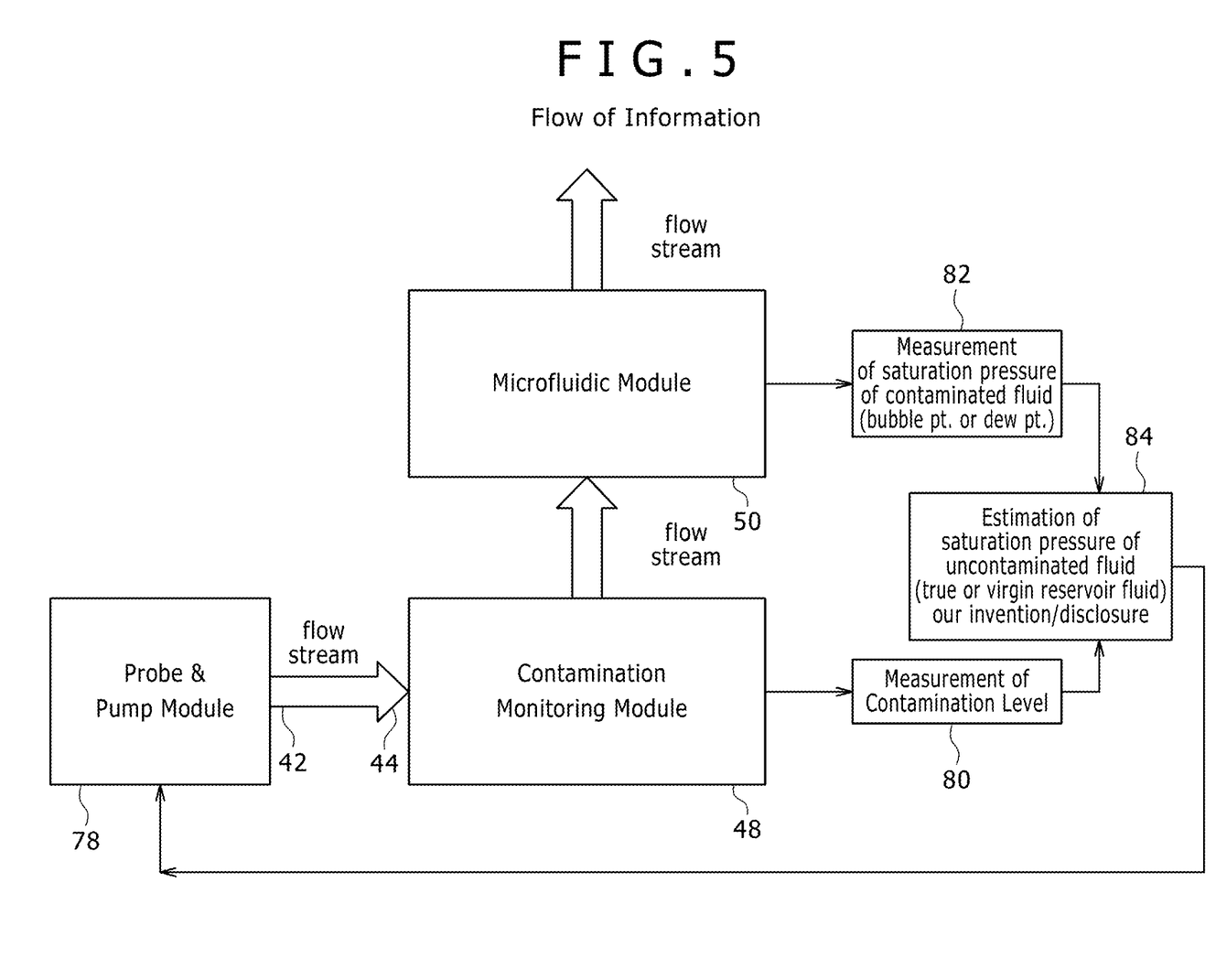
FIG. 5 is an illustration of a workflow regarding fluid sample data collection and analysis as the fluid sample flows through the sampling system downhole, according to an embodiment of the disclosure.

Referring generally to FIG. 5, an example of a workflow utilizing sampling system 22 for downhole, in situ analysis is illustrated. In this example, the sample 44 is initially moved into sampling system 22 via probe 42. By way of example, probe 42 may be part of a pump module 78 used to pump the fluid sample 44 from the surrounding reservoir 30 and into sampling system 22. From probe 42, the fluid sample 44, e.g. oil sample, flows into contamination monitoring module 48 where the sample 44 is analyzed to provide measurement data indicating a contamination level as referenced by block 80 of the workflow. The sample 44 continues to flow through sampling system 22 and into microfluidic module 50 where the sample 44 is further analyzed to provide data related to a desired phase transition property of the sample 44. For example, the microfluidic module 50 may be used to obtain data related to a measurement of saturation pressure of a contaminated fluid, e.g. bubble point pressure or dew point pressure, as indicated by block 82.

The contamination related data (see block 80) and the phase transition property data of the contaminated sample obtained from microfluidic module 50 (see block 82) are then further processed via, for example, downhole processor 36 and/or surface processing system 38. The further processing of data from module 48, 50 enables an accurate estimation of the desired phase transition property of the uncontaminated sample fluid, e.g. a saturation pressure of uncontaminated fluid, to obtain the desired phase transition property of the virgin reservoir fluid, as indicated by block 84. Based on the processing results, the sample 44 may be discharged to, for example, dump line 52/sample capture chamber 54 or the sample may be recirculated to probe 42 and through modules 48, 50 for further iterative processing.

In implementing the sampling procedure and analysis via modules 48, 50 in combination with downhole processor 36 and/or surface processing system 38, a mixture of well operation procedures, measurements, and analysis processes are used to accurately determine the desired phase transition property. For example, the overall procedure and analysis may be used to determine the bubble point pressure of virgin crude oil residing in reservoir/formation 30. The determination may be made in spite of the presence of contaminants in the virgin crude oil, e.g. drilling mud, and without withdrawing samples from the wellbore for laboratory analysis.

The sampling procedure and analysis also may be used to infer the presence of complete fluid zones above or below a given horizon not intersected by the well trajectory. Examples include the inference of a condensate column beneath the gas reservoir (which may suggest deepening of the well) which corresponds with the depth at which an increasing trend of formation pressure with depth will equal a true dew point pressure. The sampling procedure and analysis also may be employed to reveal vertical gradations of a hydrocarbon column; discontinuities, e.g. baffles, barriers; anomalies, e.g. decreasing density with depth and phase inversion; and a host of other complex, geologically-induced and thermodynamically-manifested reservoir configurations. This expanded knowledge provided by the sampling procedure and analysis can be used to improve well related procedures, e.g. reservoir evaluation, conceptualization of recovery strategies, and elaboration of an appropriate field development program.

The sampling system 22 may utilize various types of modules, e.g. modules 48, 50, to obtain the desired downhole analysis of the fluid samples 44. Each module also may have various configurations of selected sensors to facilitate the analysis. By way of example, the microfluidic module 50 may be structured as a measurement module using a capillary flow diversion through the microfluidic line 68. It should be noted that in some embodiments, a hydrophobic membrane may be utilized to remove water from the fluid sample 44. The hydrophobic membrane may be positioned along the flow path through sampling system 22 so as to allow passage of hydrocarbon fluids while blocking water phase, thus blocking flow of water phase into microfluidic line 68. The remaining hydrocarbon fluids flow through sensors 64 until reaching depressurization chamber 76. The hydrophobic membrane or membranes may be used to block flow of water into one or both of the modules 48, 50.

The depressurization chamber 76 entraps a small amount of the sample fluid for controlled depressurization to stimulate bubble formation. Thermal energy, e.g. thermal bursts, also may be employed to stimulate the bubble formation in some applications. The sensor 74 or other suitable measurement apparatus in combination with suitable pressure sensors 34 may be used to determine the pressure at which created bubbles persist in equilibrium within the oil phase. Following depressurization, the fluid in depressurization chamber 76 may be flushed to enable depressurization and measurement of subsequent samples as the well procedure, e.g. a well cleanup procedure, proceeds. Other sensors, e.g. sensor 70 and 72, may be used to measure density, viscosity, or other desired properties to facilitate the analysis.

In the illustrated embodiment of sampling system 22, the contamination monitoring module 48 is positioned and constructed to enable correction of fluid sample 44 with respect to the presence of contaminants. In well operations in which oil-based mud is used during drilling, for example, the contamination monitoring module 48 may be used to correct for the presence of this non-native reservoir fluid in the sample 44. Because a contaminant such as oil-based mud is a hydrocarbon fluid, the mixture of native reservoir crude oil and oil-based mud in sample 44 is able to pass through water blocking membranes in sampling system 22. Without correction, the bubble point pressure of the sample 44 ends up being the bubble point pressure of the contaminated reservoir fluid sample.

A contaminated oil sample tends to have a lower bubble point pressure than the virgin reservoir fluid. Testing has shown a decrease in the bubble point pressure proportional to the level of contamination in the sample. For example, each additional 1% of contamination in volumetric terms results in reservoir fluids exhibiting a depression in bubble point pressure ranging from approximately 0.5% to 1.5% compared to native or virgin crude oil. Therefore, oil having a true or virgin bubble point pressure of 4000 psi but contaminated at 10% volume with oil-based mud can have a bubble point pressure depression of 200-600 psi. For heavier oil, this range can be even broader.

Accordingly, the sampling system 22 utilizes contamination monitoring module 48 to correct for contamination so as to improve assessment of the vertical definition of a hydrocarbon column. Each well zone associated with a corresponding station 32 may have a different level of contamination, but sequential sampling and contamination correction via module 48 may be used to obtain a true bubble point pressure profile (or other phase transition property profile). Consequently, the in situ analysis can be used to obtain an accurate fluid model representing selected vertical intervals thus enabling accurate volumetric assessment of: oil-in-place, recovery behavior, well productivity, depletion process, and/or other well operation attributes.

The data collection procedures and data analysis may be performed in situ at desired downhole locations by uniquely utilizing the combined systems of contamination monitoring module 48 and microfluidic module 50 in downhole sampling system 22. Depending on the application, the contamination monitoring module 48 may obtain measurements utilizing one or two flow lines in the sampling system 22 along well string 28. The use of two flow lines may be referred to as focused sampling and may employ two autonomous pumps for moving the sample 44 through the module 48. In other applications, the contamination monitoring module 48 may employ an unfocused sampling approach using a single flow line and pump to obtain an estimation of the contamination level.

Sample contamination determination, however, is mathematically an under-determined or ill-pose problem. By way of explanation: in a forward sense, if two fluids are known and mixed in a certain portion and properties of the resulting mixture are measured, the mixing proportion of the two fluids can be determined with high precision. In an inverse sense, however, measuring the properties of an existing mixture (e.g. contaminated oil) leads to a range of possible answers with respect to the contamination level depending on what is presumed to be the characteristics of the native fluid even if the property of one of the fluids is known.

For example, the properties of the filtrate resulting from seepage of the oil-based mud into the formation may be known and, in some applications, may be identical to a base oil used to make up the oil-based mud. This problem is known as the end-point indeterminacy problem. Because we do not know the precise nature of the native fluid (which is one of the "endpoints"), the contamination level is not known even if the precise nature of the contaminating filtrate is known. However, use of sampling system 22 enables sufficiently accurate estimation of the contamination level to provide a useful in situ analysis. In fact, the in situ contamination level estimation via sampling system 22 is sufficiently comparable to what can be obtained in a laboratory setting.

By way of example, testing in a laboratory setting may yield results in determining contamination with an accuracy level of 1% to 2% and the in situ analysis provided by the sampling system 22 described herein yields similar results. With this level of accuracy regarding determination of contamination of the sample, the in situ analysis procedure can be used to correct for the measured phase transition property, e.g. apparent bubble point pressure, to obtain the proper phase transition property, e.g. true bubble point pressure, of the virgin reservoir fluid during formation sampling operations.

According to an embodiment of one operational procedure, apparent bubble point pressure is measured at successive stages of a formation cleanup operation while respecting certain operational constraints. For example, the measurements may be commenced shortly after a water phase fraction in the flow line drops below a water entry threshold of a hydrophobic membrane, e.g. 30%, to ensure a water-free (or water-reduced) effluent downstream of the membrane. Depending on the configuration of sampling system 22, commencing measurement may involve a valving procedure to divert the stream of sample fluid 44 from the primary flow line 66 to the microfluidic line 68.

In this procedure, the fluid sample 44 is directed along microfluidic line 68 and undergoes a sequence of depressurization and thermal pulsation to ensure a repeatable bubble point pressure measurement. The microfluidic line 68 is thoroughly flushed once a stable bubble point pressure is obtained and this process may be repeated many times during cleanup. The timing of the repeated flushing may be set based on a pace of contamination decay during the cleanup operation and continued until such time as an operator is ready to collect a fluid sample or samples at the selected station/interval 32. Subsequently, the sampling system 22 may be moved to the next station/interval 32. This type of operational sequence may be achieved by utilizing a two-way information flow, e.g. feedback system, between the contamination monitoring module 48 and the microfluidic module 50.

Depending on the application, the two-way information flow may be realized by using varying degrees of manual intervention and automation. An example of one approach for implementation of the procedure involves a semi-manual/semi-automated process which may be similar to such practices in the industry for optimizing formation sampling operations. The near-borehole flow in the cleanup phase of a well operation tends to be complex and governed by a diverse set of knowable and unknowable as well as controllable and uncontrollable factors related to formation anisotropy, vertical inter-zonal flow, formation dip and bedding, borehole deviation, viscosity contrast of native and non-native fluids, depth of invasion, flow conditioning geometries of the probe (and/or packer), pumping rates, and phase transition events that may be triggered during the flow process. As a result, automated control over part or all of the process is helpful in maintaining consistency and accuracy during the formation sampling operations. For example, the processing of contamination data (see block 80 in FIG. 5) and phase transition property data of the contaminated sample (see block 82 in FIG. 5) to estimate the corresponding phase transition property of uncontaminated fluid (see block 84 in FIG. 5) may be performed automatically via, for example, downhole processor 36 and/or surface processor system 38.

According to an embodiment, one type of analysis procedure employed by sampling system 22 (and corresponding processor) may be referred to as a multi-point method. According to the multi-point method, prior knowledge is utilized to determine the level of contamination including a recognition that bubble point pressure is reduced with increasing contamination and that the nature of decay depends on the nature of the crude oil and the oil filtrate causing the depression in bubble point pressure. For example, it is known that oil-based muds in general cause a near linear drop in bubble point pressure but non-synthetic oil-based mud, e.g. diesel, shows linearity over a wider range of contamination levels. This results from the non-synthetic oil-based mud being more similar to the native oil as compared to synthetic oil which exhibits linearity in a narrower/lower range of contamination level.

In this embodiment, the sampling system 22 utilizes this analysis procedure based on the physical property of oil-oil mixtures (the degassed oil causing bubble point pressure depression of the live or gassy oil) and uses a set of bubble point pressure-while-cleanup measurements described above to infer a bubble point pressure at the limiting case of zero contamination. Because a spread or uncertainty is associated with each contamination level, as may be obtained from standard industry procedures, there is a mathematical relationship between uncertainty of successive contamination levels. This leads to the intuitive conclusion that uncertainty in contamination is proportional to contamination. Thus, the multi-point method enables quantification of the uncertainty associated with the true bubble point pressure estimated according to this procedure.

According to another embodiment, an equation-of-state (EOS) analysis procedure may be employed by the sampling system 22 and corresponding processor(s). According to the EOS analysis procedure, a thermodynamic model is used which assumes that if the chemical composition of simple fluids is known the physical properties of those fluids may be inferred. For example, if the chemical composition of a simple natural gas, e.g. dry gas with no non-hydrocarbon components, is known then its physical properties, e.g. density and compressibility, may be computed for a range of pressure/temperature conditions. With the EOS analysis procedure, an assumption also is made that if the chemical composition and certain physical properties are known for less simple fluids, the remaining physical properties can be inferred.

When using the EOS analysis procedure via sampling system 22 and the corresponding processor(s), composition data available from the contamination monitoring module 48 may be used to infer remaining physical properties, e.g. bubble point pressure. By way of example, the contamination monitoring module 48 may be used to obtain composition data from the optical spectrum of the contaminated crude oil sample 44. The contamination monitoring module 48 also may be used to determine in situ measurements of other physical properties, e.g. density, and this may be combined with the composition data to determine the remaining physical property, e.g. bubble point pressure. In some embodiments, the composition data can be further calibrated based on prior knowledge which may be stored in a corresponding database or other storage system.

Comparison of this computed bubble point pressure with the actual measured bubble point pressure at microfluidic module 50 enables calibration of the thermodynamic parameters inherent in the EOS model to thus minimize potential mismatch, e.g. a binary interaction coefficient/acentric factor may be adjusted to provide a better match. This enables an estimation of the true bubble point pressure of the native oil when given an estimation of the contamination level via the contamination monitoring module 48.

Furthermore, the estimation of true bubble point pressure of the live or native oil may be cross checked against the estimation obtained via the multi-point method described above, particularly if several snapshots of bubble point pressure are obtained during the well cleanup operation. In some embodiments, additional iterations may be performed via both the multi-point method and the EOS procedure to provide greater agreement and coherency. Because these two different methods are used in this embodiment and because the EOS procedure can utilize multiple "snapshots" of the cleanup process, the degrees of freedom of the analysis are substantially reduced and this leads to more consistent, coherent, and robust results.

The in situ analysis procedure described herein may be used to determine useful phase transition properties of a native reservoir fluid. For example, the vertical distribution of a given phase transition property, e.g. bubble point pressure, may be determined across the fluid column based on a succession of measurements taken at a plurality of stations 32 along borehole 24. Additionally, inferences may be drawn about regions of the reservoir which have not been intercepted by the well trajectory, e.g. regions below and/or above the intersected reservoir interval. Accurate measurements of the desired phase transition property may be obtained via sampling system 22 without the delay of performing laboratory experiments.

Depending on the application, the measurement and analysis procedure implemented by the downhole sampling system 22 may utilize a focused sampling method with dual line measurements to infer the contamination level with fewer degrees of freedom. However, an unfocused sampling method using a single line measurement may be used for many types of applications. In some applications, processing of the contamination monitoring module data may be facilitated by determining composition of the mud filtrate used at a well site via, for example, portable gas chromatography units.

Subsequently, the multi-point method and the EOS procedure may both be applied via downhole sampling system 22 and the corresponding processor (e.g. downhole processor 36 and/or surface processing system 38) to obtain an accurate estimation of the true bubble point pressure (or other phase transition property) of the native reservoir fluid. The ability to use in situ data collection and analysis enables a rapid and robust estimation of true bubble point pressure (or other phase transition property) and its associated spread.

Depending on the parameters of a given application and/or environment, the sampling system 22 may comprise a variety of structures and components. For example, the sampling system 22 may comprise various modules for obtaining the desired data used to enable the downhole fluid analysis and the computational procedure described herein. In some embodiments, the sampling system 22 utilizes contamination monitoring module 48 with a variety of sensors to obtain desired fluid sample property related data for processing to determine the true phase transition property of the reservoir oil at various stations along the borehole.

Similarly, the microfluidic module 50 may comprise a variety of sensors which work in cooperation with the depressurization chamber 76 to obtain the desired data used to compute the true bubble point pressure or other phase transition property. Module 48 and/or module 50 may comprise or may work in cooperation with pressure and temperature sensors 34. The sampling system 22 also may be used with a variety of well strings 28 and other well systems. The data obtained and analyzed via sampling system 22 may be further processed according to the computational methodology described herein at a suitable downhole location and/or surface location.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method for downhole fluid analysis, comprising:
deploying a sampling system downhole in a borehole located within a reservoir containing oil;
using the sampling system to obtain samples of the oil at a plurality of stations along the borehole;
analyzing each sample of the oil in situ via a contamination monitoring module of the sampling system to obtain contamination data to correct for contamination of the oil resulting from the presence of a non-native reservoir fluid, wherein the contamination data is at least partially based on sensor data from a first viscosity sensor, a first density sensor, a first optical sensor, or a combination thereof, in the contamination monitoring module;
analyzing each sample of the oil in situ via a microfluidic measurement module of the sampling system to obtain, independent from the contamination data, a phase transition property of the oil having the contamination, wherein the phase transition property is at least partially based on sensor data from a depressurization chamber and at least one of a second density sensor, a second viscosity sensor, a second optical sensor, or a combination thereof, in the microfluidic measurement module; correcting the phase transition property with the contamination data to obtain a true phase transition property of the oil without the contamination in each sample of the oil; and
recirculating each sample of the oil through the contamination monitoring module and the microfluidic measurement module for iterative processing comprising the analyzing to obtain the contamination data, the analyzing to obtain the phase transition property, and the correcting to obtain the true phase transition property.

2. The method as recited in claim 1, comprising determining changes in the true phase transition property between stations of the plurality of stations along the borehole to obtain a true phase transition property profile across the plurality of stations.

3. The method as recited in claim 1, wherein the contamination monitoring module comprises the first optical sensor and at least one of the first viscosity sensor or the first density sensor, and the first optical sensor comprises an optical spectroscopy sensor.

4. The method as recited in claim 1, wherein analyzing each sample of the oil in situ via the microfluidic measurement module comprises placing each sample of the oil in the depressurization chamber to cause a phase transition.

5. The method as recited in claim 1, wherein each of the phase transition property and the true phase transition property comprises a bubble point pressure or a dew point pressure.

6. The method of claim 1, wherein the contamination monitoring module comprises the first viscosity sensor, the first density sensor, and the first optical sensor comprising a first optical spectroscopy sensor in the contamination monitoring module.

7. The process of claim 1, wherein the microfluidic module comprises the depressurization chamber, the second density sensor, the second viscosity sensor, and the second optical sensor comprising a second optical spectroscopy sensor.

8. A system, comprising:
a well string comprising a sampling system configured to be deployed downhole in a wellbore located within a reservoir containing oil, wherein the sampling system is configured to obtain samples of the oil, and the sampling system comprises:
a contamination monitoring module configured to analyze each sample of the oil to obtain contamination data to correct for contamination of the oil resulting from the presence of a non-native reservoir fluid, wherein the contamination data is at least partially based on sensor data from a first viscosity sensor, a first density sensor, a first optical sensor, or a combination thereof, in the contamination monitoring module;
a microfluidic measurement module configured to analyze each sample of the oil to obtain, independent from the contamination data, a phase transition property of the oil having the contamination, wherein the phase transition property is at least partially based on sensor data from a depressurization chamber and at least one of a second density sensor, a second viscosity sensor, a second optical sensor, or a combination thereof, in the microfluidic measurement module;
a processor configured to correct the phase transition property with the contamination data to obtain a true phase transition property of the oil without the contamination in each sample of the oil; and
a recirculation flow path through the contamination monitoring module and the microfluidic measurement module to enable iterative processing to obtain the contamination data via the contamination monitoring module, the phase transition property via the microfluidic measurement module, and the true phase transition property via the processor.

9. The system as recited in claim 8, wherein the contamination monitoring module comprises the first viscosity sensor, the first density sensor, and the first optical sensor comprising a first optical spectroscopy sensor.

10. The system as recited in claim 9, wherein the microfluidic measurement module comprises the depressurization chamber, the second density sensor, the second viscosity sensor, and the second optical sensor comprising a second optical spectroscopy sensor.

11. The system as recited in claim 8, wherein the processor is positioned downhole as part of the well string.

12. The system as recited in claim 8, wherein the sampling system is configured to determine changes in the true phase transition property between a plurality of stations along the wellbore to obtain a true phase transition property profile across the plurality of stations.

13. The system as recited in claim 12, wherein the processor is configured to use the true phase transition property profile to obtain a fluid model across the plurality of stations.

14. The system as recited in claim 8, wherein a flow path of the oil passes through the contamination monitoring module followed by the microfluidic measurement module in a series arrangement.

15. The system as recited in claim 8, wherein the processor is further configured to use an equation of state model in conjunction with the microfluidic measurement module to calibrate a set of thermodynamic parameters in the equation of state model, wherein the equation of state model with the set of thermodynamic parameters is capable of producing an estimation with the contamination data.

16. The system of claim 8, wherein the contamination monitoring module and the microfluidic measurement module are commonly housed in a sampling system structure.

17. The system of claim 16, wherein the processor is directly coupled to the sampling system having the sampling system structure.

* * * * *